(12) United States Patent
Berman et al.

(10) Patent No.: US 7,022,630 B2
(45) Date of Patent: Apr. 4, 2006

(54) NONWOVEN PROTECTIVE FABRICS WITH CONDUCTIVE FIBER LAYER

(75) Inventors: Mark Henry Samuel Berman, Greenville, SC (US); Samuel Charles Baer, Greenville, SC (US)

(73) Assignee: BBA Nonwovens Simpsonville, Inc., Simpsonville, SC (US)

( * ) Notice: Subject to any disclaimer, the term of this patent is extended or adjusted under 35 U.S.C. 154(b) by 72 days.

(21) Appl. No.: 10/691,015

(22) Filed: Oct. 22, 2003

(65) Prior Publication Data

US 2004/0127132 A1 Jul. 1, 2004

Related U.S. Application Data

(60) Provisional application No. 60/420,496, filed on Oct. 23, 2002.

(51) Int. Cl.
B32B 9/00 (2006.01)

(52) U.S. Cl. .................. 442/365; 442/382; 442/400; 442/401; 442/414; 428/903

(58) Field of Classification Search ............... 442/365, 442/382, 400, 401; 428/903
See application file for complete search history.

(56) References Cited

U.S. PATENT DOCUMENTS

| | | | |
|---|---|---|---|
| 3,666,550 A | 5/1972 | Okuhashi et al. | |
| 4,217,386 A * | 8/1980 | Arons et al. | 428/198 |
| 4,766,029 A | 8/1988 | Brock et al. | |
| 4,902,562 A | 2/1990 | Bahia | |
| 5,324,579 A | 6/1994 | Sassa et al. | |
| 5,368,913 A | 11/1994 | Ortega | |
| 5,384,185 A | 1/1995 | Bovenschen et al. | |
| 5,484,645 A | 1/1996 | Lickfield et al. | |
| 5,614,306 A | 3/1997 | Jobe et al. | |
| 5,766,737 A | 6/1998 | Willey et al. | |
| 5,883,026 A | 3/1999 | Bowen, Jr. et al. | |
| 6,245,694 B1 | 6/2001 | Davenport et al. | |
| 6,730,622 B1 * | 5/2004 | Curro et al. | 442/336 |
| 6,808,791 B1 * | 10/2004 | Curro et al. | 428/198 |
| 2001/0000769 A1 | 5/2001 | Bhattacharjee et al. | |

FOREIGN PATENT DOCUMENTS

| | | |
|---|---|---|
| EP | 0 399 397 A | 11/1990 |
| EP | 0 602 613 A | 6/1994 |
| WO | WO 96/28597 A | 9/1996 |
| WO | WO 98/04767 A | 2/1998 |
| WO | WO 02/50347 A | 6/2002 |

* cited by examiner

*Primary Examiner*—Terrel Morris
*Assistant Examiner*—Arden B. Sperty
(74) *Attorney, Agent, or Firm*—Alston & Bird LLP

(57) ABSTRACT

Nonwoven barrier laminates are provided having a desirable balance of properties, including barrier properties, strength, static dissipation, fluid repellency, aesthetics and tactile properties. The nonwoven barrier laminates of the invention generally include outer spunbonded layers, at least one hydrophobic microporous layer between the outer spunbonded layers, and at least one discrete layer of electrically conductive strands. A multiplicity of discrete bond sites bond the various layers of the nonwoven barrier laminate into a coherent fabric.

15 Claims, 3 Drawing Sheets

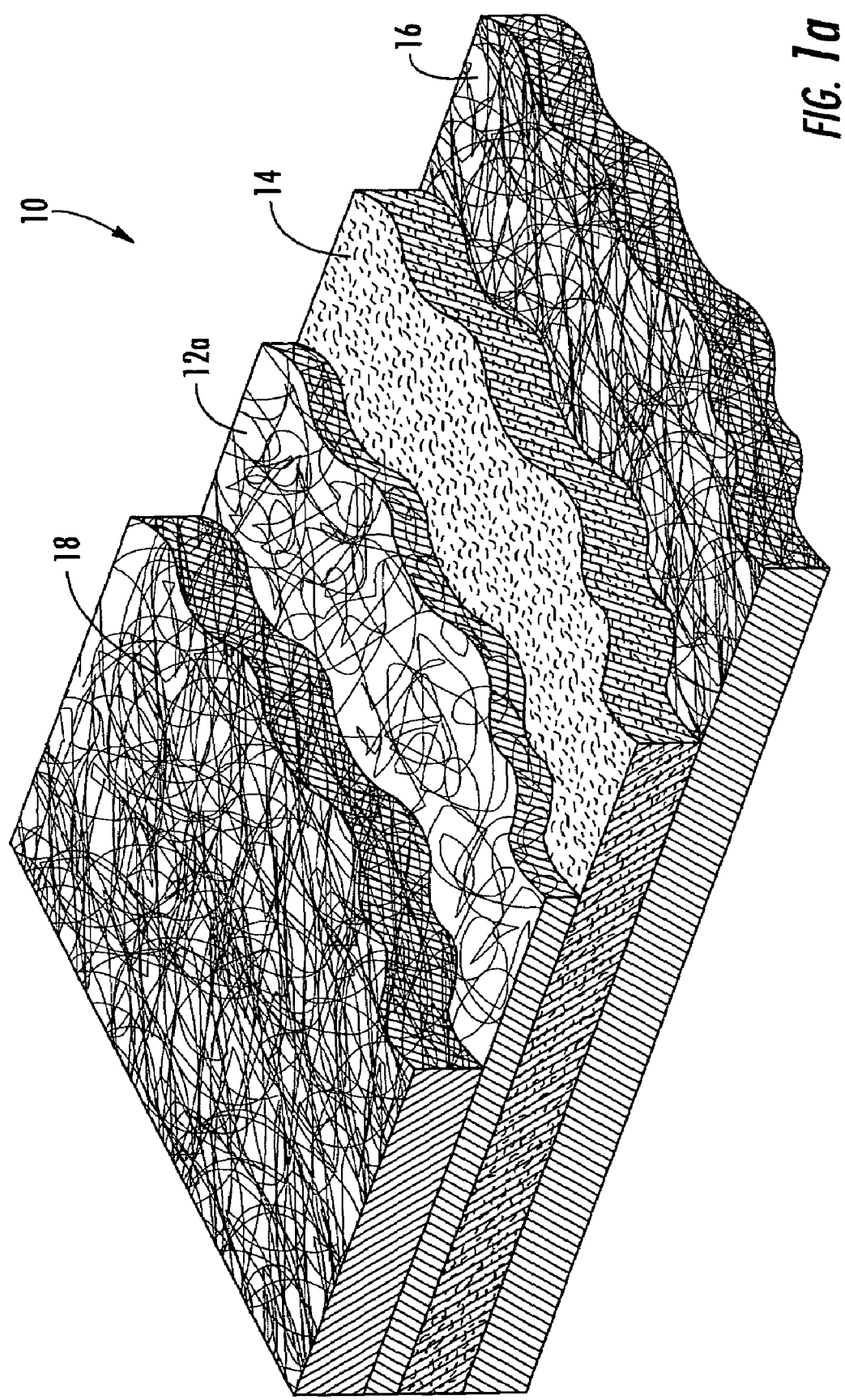

NONWOVEN PROTECTIVE FABRICS WITH CONDUCTIVE FIBER LAYER

CROSS-REFERENCE TO RELATED APPLICATION

This application claims priority from U.S. provisional patent application No. 60/420,496 filed Oct. 23, 2002.

FIELD OF THE INVENTION

The present invention relates to nonwoven fabrics and to processes for producing nonwoven fabrics. More specifically, the invention relates to nonwoven barrier fabrics having a balance of liquid repellent and antistatic properties that are particularly suited for medical applications.

BACKGROUND OF THE INVENTION

Barrier fabrics have been developed which impede the passage of bacteria and other contaminants and which are used for disposable medical fabrics, such as surgical drapes, disposable gowns, sterile wrap and the like. Barrier fabrics can be formed by sandwiching an inner fibrous web of thermoplastic meltblown microfibers between two outer nonwoven webs of substantially continuous thermoplastic spunbonded filaments. The fibrous meltblown web provides a barrier impervious to bacteria or other contaminants in the composite nonwoven fabric. The outer spunbonded webs are selected to provide abrasion resistance and strength to the composite fabric. Examples of such trilaminate nonwoven barrier fabrics are described in U.S. Pat. Nos. 4,041,203 and 4,863,785.

However, in addition to barrier properties and strength, medical barrier fabrics must also advantageously provide a number of other beneficial properties. For example, barrier fabrics used in medical applications must dissipate static charge because they are often used in the presence of sensitive electronic equipment and potentially volatile gases such as ether. Medical barrier fabrics must also exhibit superior fluid repellency, so that contact by water, alcohol or other organic solvents does not impair the barrier properties of the fabric.

Both static dissipation and fluid repellency have generally been imparted to medical barrier fabrics to date by applying a series of topical treatments. More specifically, antistatic performance has been imparted to medical fabrics by the application of hydrophilic coatings. Fluid repellency has been achieved in medical fabrics by the application of hydrophobic coatings. Unfortunately, the hydrophilic and hydrophobic natures of the various topical treatments are incompatible, hence the balance of properties provided to the barrier fabric is generally compromised. For example, acceptable antistatic performance may be achieved at the sacrifice of water resistance.

Fabrics rendered antistatic by means other than topical treatments are known. For example, U.S. Pat. No. 5,368,913 to Ortega discloses spunbonded fabrics for use in carpeting and the like that include conductive filaments, such as carbon or metallic filaments, distributed throughout the fabric thickness. Such fabrics can be problematic in garment applications because the electrically conductive fiber is not isolated visually or tactilely from the wearer. Conductive filaments, such as carbon or metallic filaments, are not readily dyeable and are thus generally considered to be less aesthetically pleasing than more traditional textile fibers. Carbon and metallic filaments further lack the flexibility and softness provided by traditional textile fibers. Further, fabric constructions including conductive filaments throughout their thickness generally require a significant amount of conductive filament, resulting in increased costs. The presence of conductive filaments during web manufacture can further disable the electrostatic charges frequently applied to filaments to enhance the uniformity of nonwoven webs.

Thus there remains a need in the art for improved antistatic, fluid repellent barrier fabrics.

SUMMARY OF THE INVENTION

The invention provides nonwoven barrier laminates having a desirable balance of properties, including barrier properties, strength, static dissipation, fluid repellency, aesthetics and tactile properties. The nonwoven barrier laminates of the invention generally include outer spunbonded layers, at least one hydrophobic microporous layer between the outer spunbonded layers, and at least one discrete layer of electrically conductive strands. A multiplicity of discrete bond sites bond the various layers of the nonwoven barrier laminate into a coherent fabric.

The nonwoven barrier fabrics of the invention have excellent barrier properties, provide alcohol and water repellency, antistatic performance, are readily dyeable, are flexible and comparatively soft. The nonwoven barrier laminates of the invention can be used as components in a variety of nonwoven products, and are particularly useful in medical fabrics, such as sterile wraps, surgical gowns, surgical drapes, and the like. The spunbonded layers provide good abrasion resistance, strength and aesthetic properties to the laminate fabrics of the invention. The inner hydrophilic microporous layer provides good barrier properties. The layer of electrically conductive strands provides superior static dissipation characteristics for negative charges.

In another aspect of the invention, medical fabrics that include the nonwoven barrier laminate described above are also provided. For example, the nonwoven barrier fabrics of the invention are useful as components in medical fabrics such as surgical drapes and gowns. When used to form a surgical gown, the discrete layer of conductive filaments dissipates negative static charges as they arise, thereby decreasing both static discharge and static cling. Accordingly, the surgical gowns of the invention are formed from fabrics having greater safety and comfort, as well as superior fluid resistance and antistatic properties.

Nonwoven barrier laminates according to the invention can be readily manufactured according to another aspect of the invention. The nonwoven barrier fabrics may be manufactured by forming a layered web including outer spunbonded layers sandwiching at least one hydrophobic microporous layer and a discrete layer of electrically conductive strands. Thereafter, the layers of the resultant composite laminates are subjected to a thermal bonding treatment sufficient to introduce a plurality of discrete thermal bonds that provide cohesion to the laminate.

The nonwoven barrier laminates of the invention provide several desirable and yet apparently opposing properties in one fabric. For example, the barrier laminates of the invention provide antistatic protection without sacrifice to fluid repellency.

BRIEF DESCRIPTION OF THE DRAWINGS

In the drawings which form a portion of the original disclosure of the invention:

FIG. 1a is cut-away schematic perspective view of a laminate nonwoven fabric in accordance with one embodiment of the present invention;

DETAILED DESCRIPTION OF THE INVENTION

The present invention will now be described more thoroughly hereinafter with reference to the accompanying drawings, in which illustrative embodiments of the invention are shown. This invention may, however, be embodied in many different forms and should not be construed as limited to the embodiments set forth herein. Rather, this embodiment is provided so that the disclosure will be thorough and complete, and will convey fully the scope of the invention to those skilled in the art. Like numbers refer to like elements throughout. For purposes of clarity, the scale has been exaggerated.

Figure 1B:
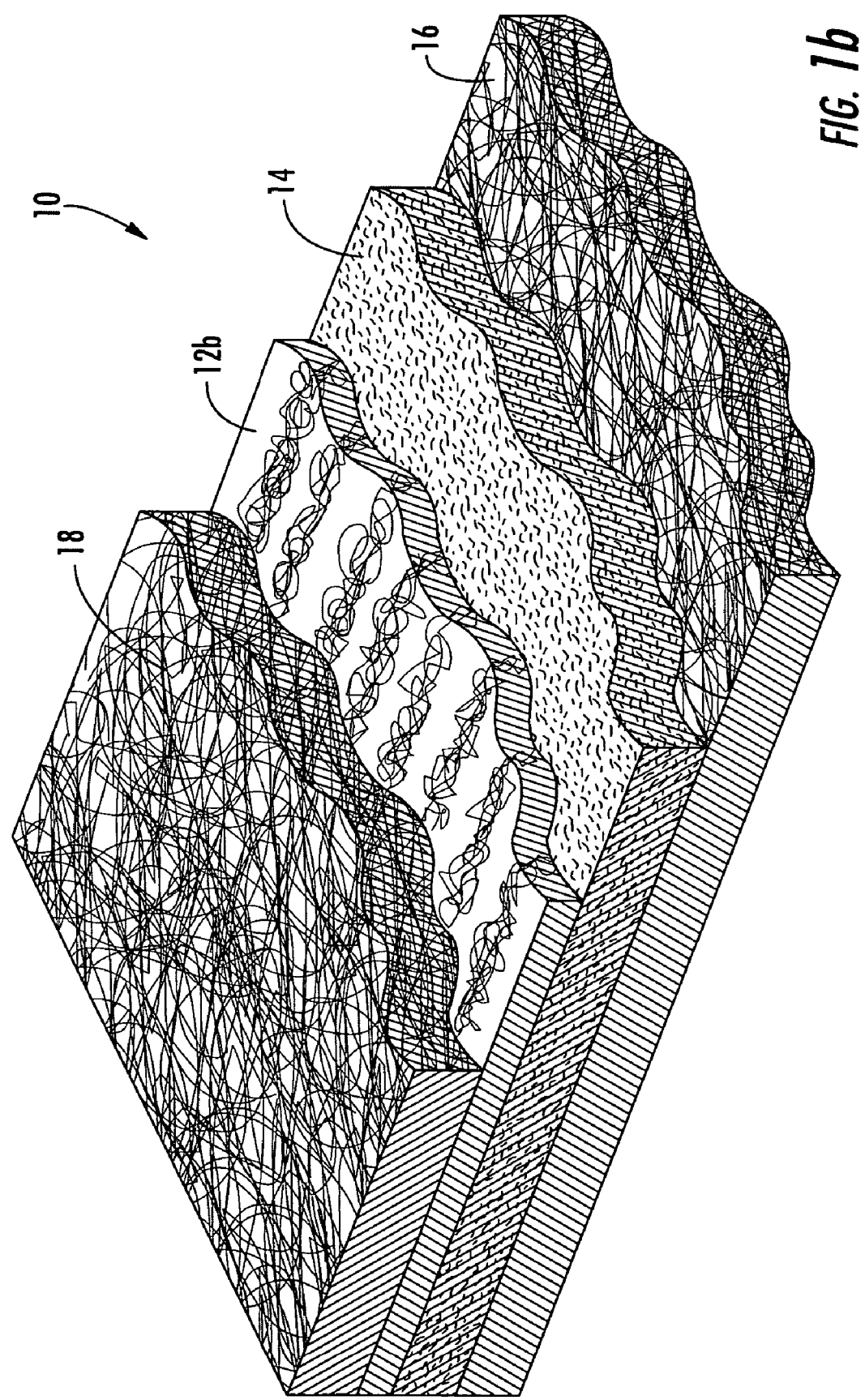
FIG. 1b is cut-away schematic perspective view of a laminate nonwoven fabric in accordance with a second embodiment of the present invention.

FIGS. 1a and 1b are schematic perspective views of a barrier laminate in accordance with two embodiments of the present invention. The barrier laminate is designated generally as 10. In the advantageous embodiments provided in FIGS. 1a and 1b, the barrier laminate 10 is a four ply composite comprising a conductive layer 12a or 12b and at least one hydrophobic microporous layer 14 sandwiched between outer plies 16 and 18. In addition to beneficial antistatic and fluid repellent properties, the barrier laminate 10 has good strength, flexibility and drape and may be formed into various articles or garments such as sterile wraps, surgical gowns, surgical drapes and the like. The barrier properties of the laminate 10 make it particularly suitable for medical applications, but the laminate is also useful for any other applications wherein a barrier to contaminants and fluid repellency, as well as a cloth-like feel and drapeability, would be desirable, such as industrial garments, filtration media, and disposable wipes.

The outer plies 16 and 18 of the barrier laminate 10 may be formed from any construction capable of providing sufficient strength and cohesion to the resulting barrier laminate 10. Advantageously, outer plies 16 and 18 of the barrier laminate 10 are nonwoven webs, such as spunbonded webs of substantially continuous nonelastomeric thermoplastic filaments. The thermoplastic filaments of outer plies 16 and 18 can be made of any of a number of known fiber forming polymers or polymer compositions. Exemplary polymers include those selected from the group consisting of polyolefins such as polypropylene and polyethylene, polyesters, polyamides, and copolymers and blends thereof. The terms "polypropylene" and "polyethylene" are used herein in a general sense, and are intended to include various homopolymers, copolymers, and terpolymers thereof. The term "polyethylene" is also intended to include any polyethylene suitable for fiber formation including low density polyethylene, high density polyethylene, and linear low density polyethylene. The thermoplastic filaments of outer plies 16 and 18 may be made from either the same or different polymers. Advantageously, the thermoplastic filaments of outer plies 16 and 18 are formed from polypropylene.

Outer plies 16 and 18 may be produced using well-known nonwoven processes, e.g. spunbonding processes, and may suitably have a basis weight in the range of about 10 gsm to 100 gsm. In advantageous embodiments, the outer plies 16 and 18 have a basis weight ranging from about 10 to 25 gsm. The basis weights of outer plies 16 and 18 may be approximately the same, or may differ. Deniers for spunbonded substantially continuous thermoplastic filaments in accordance with the invention generally range from about 2.0 to 4.0.

The hydrophobic microporous layer 14 may be any layer known in the art to provide barrier properties to laminate structures. In advantageous embodiments, the hydrophobic microporous layer 14 is a nonwoven fibrous web comprising a plurality of nonelastomeric thermoplastic meltblown microfibers. The microfibers can be made of any of a number of known fiber forming polymers or polymer compositions. Such polymers include those selected from the group consisting of polyolefins such as polypropylene and polyethylene, polyesters, polyamides, and copolymers and blends thereof. Advantageously, the microfibers are polypropylene microfibers.

The microfibers preferably have an average fiber diameter of up to about 10 microns with very few, if any, other fibers exceeding 10 microns in diameter. Typically, the average diameter of the fibers will range from 2 to 6 microns. The hydrophobic microporous layer 14 is preferably manufactured in accordance with the process described in Buntin et al., U.S. Pat. No. 3,978,185. Such meltblown fibers generally have a denier of about 1.0 or less. The hydrophobic microporous layer 14 can have a basis weight in the range of about 10 to about 80 grams per square meter (gsm), advantageously in the range of about 8 to 20 gsm.

The beneficial embodiment illustrated in FIGS. 1a and 1b, the barrier laminate 10 includes a single hydrophobic microporous layer 14. In alternative embodiments, the barrier laminate 10 includes more than a single microporous layer 14. For example, the barrier laminate 10 may include two hydrophobic microporous layers sandwiched between the outer layers 16 and 18. For embodiments including at least two hydrophobic microporous layers, the hydrophobic microporous plies may be the same or may differ. For example, the hydrophobic microporous layers may differ in composition, average denier, or basis weight. The multiple hydrophobic microporous layers may either be positioned immediately adjacent to each other or they may be arranged so as to sandwich the electrically conductive layer (12a, 12b).

The electrically conductive layer (12a, 12b) is a discrete ply that includes electrically conductive strands. As used herein, the term "strand" includes any configuration of fibrous or filamentary material including continuous filaments, staple fibers, tow or any other fibrous configuration. The electrically conductive strands within the conductive layer may be distributed within the discrete ply either anisotropically, i.e. substantially randomly throughout the fabric, as indicated in FIG. 1a by the conductive layer 12a, or the conductive strands may be arranged in a spaced apart relation from one another in zones extending generally longitudinally of the laminate as indicated in FIG. 1b by the conductive layer 12b. Although the strands of the layer 12b extend predominantly longitudinally in the machine direction, their location in the cross-machine direction may vary or fluctuate as the strands loop or double upon themselves to form generally longitudinally extending bands or zones where the strands are deposited. Typically, the conductive layer 12a or 12b is a non-cohesive ply prior to bonding the barrier laminate 10.

Suitable electrically conductive strands for use in the conductive layer include any of the electrically conductive strands known in the art, such as carbon fibers or filaments, metallic fibers or filaments, fibers or filaments made from a polymer that has electrically conductive or satic-discharging properties, and the like. As used herein the term "carbon fibers or filaments" generally refers to fibers or filaments made by heating (or "carbonizing") precursor organic fibers or filaments, such as rayon or polyacrylonitrile fibers or petroleum residues, to appropriate temperatures to convert them to primarily carbon.

The term "carbon fibers or filaments" also includes fibers or filaments made conductive by incorporating carbon into a polymeric fiber or filament structure, for example, by incorporating a core of carbon into a hollow polymer fiber or filament or by coating a fiber or filament with a sheath made of a composite containing carbon or by otherwise filling thermoplastic polymer with carbon, and the like.

The term "metallic filaments" refers to fibers made conductive by incorporating a metal into a polymeric fiber or filament structure, and includes, for example, metal plated filaments, metal-deposited filaments, metallic strands, and the like.

In advantageous embodiments of the invention, the electrically conductive strands are multicomponent filaments having at least one nonconductive polymer component and at least one conductive component. The nonconductive polymer component can be made of any of a number of known fiber forming nonelastomeric polymer or polymer composition. Such polymers include those selected from the group consisting of polyolefins such as polypropylene and polyethylene, polyesters, polyamides, and copolymers and blends thereof. The conductive component may be any material providing sufficient static dissipative properties to the conductive layer. For example, the conductive component can be derived from carbon or metal or other conductive additive. It is also possible to produce conductive monocomponent filaments by incorporating a suitable conductive melt-additive into the polymer melt during manufacture of the filaments.

In advantageous embodiments, the electrically conductive strands are multicomponent fibers that include at least one nylon component and at least one carbon component. In beneficial aspects of such embodiments, the electrically conductive strand comprises a nylon filament having one or more carbon sub-filaments attached to its perimeter, such as a nylon filament having three carbon filaments attached to its perimeter. Exemplary electrically conductive strands include filaments available from Solutia Chemical Company under the trade names NO-SHOCK™ conductive nylon; from Kanebo Ltd. under the trade name BELLTRON™; and the like. One particularly advantageous electrically conductive strand is NO-SHOCK™ conductive nylon grade 18-2-E3N. Exemplary deniers for the electrically conductive strand range from about 3 to 36 denier, such as from about 3 to 18 denier. In one advantageous embodiment, the electrically conductive strand is an 18 denier multifilament fiber having two 9 denier filaments.

Advantageously, the conductive layer is formed solely of electrically conductive strands. In alternative aspects of the invention, the conductive layer includes nonconductive strands. In such beneficial embodiments, the nonconductive strands can be made of any of a number of known fiber forming polymers and polymer compositions. Exemplary polymers include those selected from the group consisting of polyolefins such as polypropylene and polyethylene, polyesters, polyamides, and copolymers and blends thereof. The nonconductive strands are included within the conductive layer in amounts that do not interfere with the conductive nature of the layer. For example, the nonconductive strands may be included within the conductive layer in amounts of up to 10 weight percent, based on the weight of the conductive layer.

The conductive layer (12a, 12b) may be formed by any means capable of depositing a non-cohesive assembly of strands onto a moving surface. In beneficial embodiments, the conductive layer is formed by pneumatically assisted means, such as an air gun or air laying headbox.

The basis weight of the conductive layer can vary according to the degree of antistatic properties desired for the barrier laminate 10. The conductive layer generally has a basis weight ranging from about 0.01 to about 1.0 grams per square meter (gsm). In beneficial embodiments, the conductive layer has a basis weight ranging from about 0.05 to about 0.5 gsm, particularly from about 0.1 to 0.3 gsm. In one advantageous aspect of the invention, the conductive layer has a basis weight of about 0.23.

Surprisingly, barrier laminates 10 containing relatively small amounts of conductive layer can provide acceptable antistatic properties. Considered on a relative weight basis, the conductive layer generally constitutes from about 0.1 to 0.5 weight percent of the barrier laminate 10. In advantageous embodiments, the conductive layer forms from about 0.2 to 0.4 weight percent of the barrier laminate 10. In one beneficial embodiment, a conductive layer constituting about 0.37 weight percent of the barrier laminate 10 provides acceptable antistatic properties.

Layers 12a or b, 14, 16 and 18 of the barrier laminate 10 can be bonded together to form a coherent fabric using techniques and apparatus known in the art. For example, layers can be bonded together by thermal bonding, mechanical interlocking, adhesive bonding, and the like. Preferably, laminate fabric 10 includes a multiplicity of discrete thermal bonds distributed throughout the fabric, bonding layers together to form a coherent fabric.

In addition, as will be appreciated by the skilled artisan, barrier laminate 10 can include one or more additional layers to provide improved barriers to transmission of liquids, airborne contaminates and/or additional supporting layers.

Barrier laminates 10 of the invention exhibit a variety of desirable characteristics that make them particularly useful as a barrier fabrics in medical applications. The outer plies 16 and 18 are designed to provide good strength and abrasion resistance to the barrier laminate 10. The hydrophobic microporous layer 14 imparts barrier properties. The conductive layer provides acceptable static dissipation times for negative charges at no sacrifice to fluid repellency, particularly at no sacrifice to hydrostatic head. The barrier laminates of the invention can be further be treated with topical fluid repellents to provide constructions exhibiting a balance of beneficial properties, including acceptable antistatic performance at no sacrifice to water and/or alcohol repellancy.

Figure 2:
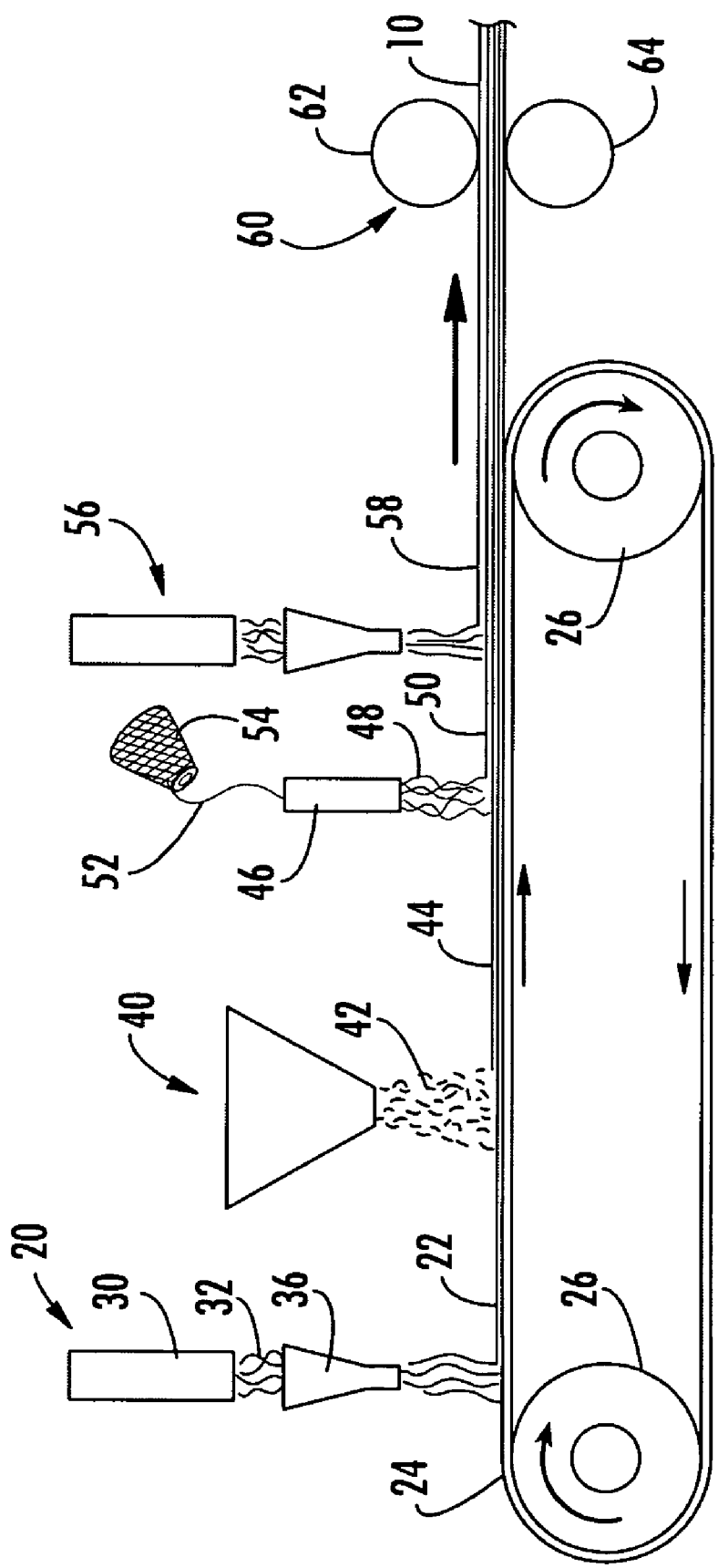
FIG. 2 schematically illustrates one method embodiment for forming a laminate nonwoven fabric of the invention.

Referring now to FIG. 2, an illustrative process for forming an advantageous embodiment of the barrier laminate 10 is illustrated. A conventional spunbonding apparatus 20 forms a first spunbonded layer 22 of substantially continuous nonconductive polymer filaments. Advantageously, the nonconductive polymer filaments are polypropylene filaments. The first spunbonded layer 22 is deposited onto a forming wire or screen 24 which is driven in a longitudinal direction by rolls 26.

The spunbonding process 20 involves extruding a polymer through a generally linear die head or spinneret 30 for melt spinning substantially continuous filaments 32. The spinneret preferably produces the filaments in substantially equally spaced arrays and the die orifices are preferably from about 0.002 to about 0.040 inches in diameter.

The substantially continuous filaments 32 are extruded from the spinneret 30 and subsequently quenched by a supply of cooling air. The filaments are directed to an attenuator 36 after they are quenched, and a supply of attenuation air is admitted therein. Although separate quench and attenuation zones may be employed, it will be apparent to the skilled artisan that the filaments can exit the spinneret 30 directly into an attenuator 36 where the filaments can be quenched, either by the supply of attenuation air or by a separate supply of quench air.

The attenuation air may be directed into the attenuator 36 by an air supply above the entrance end, by a vacuum located below the forming wire or by the use of eductors integrally formed in the attenuator. The air proceeds down the attenuator 36, which narrows in width in the direction away from the spinneret 30, creating a venturi effect and providing filament attenuation. The air and filaments exit the attenuator 36, and the filaments are collected on the collection screen 24. The attenuator 36 used in the spunbonding process may be of any suitable type known in the art, such as a slot draw apparatus or a tube type (Lurgi) apparatus.

After the spunbonded layer 22 is deposited onto screen 24, the web moves longitudinally beneath a conventional meltblowing apparatus 40. Meltblowing apparatus 40 forms a meltblown fibers stream 42 of nonconductive polymer which is deposited on the surface of the spunbonded web 22 to form a spunbonded web/meltblown web structure 44. Advantageously, the meltblown fibers stream 42 is formed from polypropylene. Meltblowing processes and apparatus are known to the skilled artisan and are disclosed, for example, in U.S. Pat. No. 3,849,241 to Buntin et al. and U.S. Pat. No. 4,048,364 to Harding et al.

In meltblowing, thermoplastic resin is fed into an extruder where it is melted and heated to the appropriate temperature required for fiber formation. The extruder feeds the molten resin to a special meltblowing die. The die arrangement is generally a plurality of linearly arranged small diameter capillaries. The resin emerges from the die orifices as molten threads or streams into high velocity converging streams of heated gas, usually air. The air attenuates the polymer streams and breaks the attenuated stream into a blast of fine fibers which are collected on a moving screen placed in front of the blast. As the fibers land on the screen, they entangle to form a cohesive web.

After the meltblown fibers stream 42 is deposited on the surface of the spunbonded web 22, the spunbonded web/meltblown web structure 44 moves longitudinally beneath an array of air guns 46 which stretches across the width of the web. For example, one or more rows of air guns 46 may extend across the width of the web. In advantageous embodiments, the air guns within the array are spaced from about 6 to 12 inches apart.

Each air gun 46 in the array deposits a discrete layer of preformed conductive strands 48, in the form of continuous filaments, provided on a package 54 onto the surface of the spunbonded web/meltblown web structure 44. The air gun 46 may advantageously be a Lurgi apparatus, commonly employed in spunbonding. However, in contrast to their use in attenuating spundonded fibers issuing from a die, the air gun 46 would not be expected to attenuate the preformed conductive filament, but merely transport it. The transport air may be directed into the air gun 46 by an air supply above its entrance end, by a vacuum located below the forming wire or by the use of eductors integrally formed in the air gun. The volume of air required to deposit the conductive filament may vary depending upon the air gun configuration. Typically, a volume of air sufficient to achieve a filament velocity of about 1000 to 3000 mpm is employed. Each air gun 46 generally deposits conductive strand onto the spunbonded web/meltblown web structure 44 at a rate ranging from about 1 to 3 grams/minute.

FIG. 2 illustrates the use of an air gun 46 to transport a single end of conductive strand 52. In alternative embodiments, a single air gun 46 may be used to simultaneously deposit multiple ends of conductive strand 52 onto the surface of the spunbonded web/meltblown web structure 44. In such embodiments, the multiple ends may be fed from packages hung on a creel or the like. In alternative aspects of the invention, the conductive filament may be deposited using a slot die. In further alternative aspects of the invention, the conductive filament may be formed in-line by means such as spunbonding or meltblowing.

Spunbonded web/meltblown web/conductive layer structure 50 is next conveyed by forming screen 24 in the longitudinal direction beneath a second conventional spunbonding apparatus 56. The spunbonding apparatus 56 deposits a second spunbonded nonconductive polymer layer onto the structure 50 to thereby form a laminate structure 58 comprising a spunbonded web/meltblown web/conductive filament ply/spunbonded web structure 58. Advantageously, the second spunbonded layer is formed from polypropylene.

The four-layer laminate 58 is conveyed longitudinally as shown in FIG. 2 to a conventional thermal fusion station 60 to provide a bonded barrier laminate 10. The fusion station 60 is constructed in a conventional manner as known to the skilled artisan, and advantageously includes cooperating embossing rolls 62 and 64, which may include at least one point roll, helical roll, and the like. Preferably, the layers are bonded together to provide a multiplicity of thermal bonds distributed throughout the laminate fabric. Bonding conditions, including the temperature and pressure of the bonding rolls, are known in the art for differing polymers. For composites comprising a polypropylene spunbonded web/ polypropylene meltblown web/conductive strand ply/ polypropylene spunbonded web, the embossing rolls are preferably heated to a temperature between about 120° C. and about 130° C. The laminate is fed through the embossing rolls at a speed of about 3 to 300 meters per minute, such as a speed between about 5 and 150 meters per minute.

Although a thermal fusion station in the form of bonding rolls is illustrated in FIG. 2, other thermal treating stations such a ultrasonic, microwave or other RF treatment zones which are capable of bonding the fabric can be substituted for the bonding rolls of FIG. 2. Such conventional heating stations are known to those skilled in the art and are capable of effecting substantial thermal fusion of the nonwoven webs. In addition, other bonding techniques known in the art can be used, such as hydroentanglement of the fibers, needling, and the like. It is also possible to achieve bonding through the use of an appropriate bonding agent as is known in the art, singly or in combination with thermal fusion.

The resultant barrier laminate 10 exits the thermal fusion station and is wound up by conventional means on a roll.

The method illustrated in FIG. 2 is susceptible to numerous variations. For example, the conductive strand 52 may be deposited directly onto the spunbonded layer 22. In such embodiments, the meltblown fibers stream 42 is subsequently directed onto the conductive layer and a second spunbonded layer applied.

Further, although the schematic illustration of FIG. 2 has been described as forming a spunbonded web directly during an in-line continuous process, it will be apparent that the spunbonded webs can be preformed and supplied as rolls of preformed webs. Similarly, although the meltblown web is shown as being formed directly on the spunbonded web, and the spunbonded web thereon, meltblown webs and spunbonded webs can both be preformed and such preformed webs can be combined with a conductive filament layer to form the laminate fabric. Alternatively, preformed spunbonded and meltblown webs can be passed through heating rolls for further consolidation, a layer of conductive filaments deposited thereon and thereafter a spunbonded layer may be extruded onto the surface of the conductive filament layer. Similarly, the four-layer laminate can be formed and stored prior to bonding.

One or more topical treatments is typically applied to the bonded barrier laminate 10. Such topical treatments and their methods of application are known in the art and include, for example, alcohol and water repellency treatments and the like, applied by spraying, dipping, etc. Fluorocarbon chemicals to enhance alcohol and water repellency are known. One example of such a topical alcohol/water repellency treatment is the application of Spinrite 150 by Fiber Sciences of Fountain Inc. S.C., a proprietary chemical treatment. It is important that nay treatments applied to the material be low in formaldehyde or other volatile materials since they will be in close contact with people during most applications.

Additionally, the polymers used in the present invention may be specifically engineered to provide or improve a desired property in the laminate. For example, any one of a variety of adhesive-promoting, or "tackifying" agents, such as ethylene vinyl acetate copolymers, may be added to the polymers used in the production of any of the webs or plies of the laminate structure to improve inter-ply adhesion. Further, at least one of the webs or plies may be treated with a treatment agent to render any one of a number of desired properties to the fabric, such as flame retardancy, hydrophilic properties, and the like.

Surprisingly, the barrier laminates of the invention can provide superior antistatic performance in comparison to conventional antistatic barrier fabrics. The typical maximum static decay time specified by medical gown converters is 0.5 seconds or less. The static decay time of conventional topically treated antistatic barrier laminates ranges from about 0.2 to 0.4 seconds. In contrast, the barrier laminates of the invention are capable of static decay times of about 0.1 seconds, particularly for negative charges. The advantageous antistatic properties of the invention are further provided at no sacrifice to the remaining laminate properties. In particular, the present invention imparts antistatic properties to barrier laminates without detrimentally affecting the fluid repellent properties of the fabric, especially the water resistance.

The present invention will be further illustrated by the following non-limiting examples.

Comparative Examples 1 Through 5

The antistatic and fluid repellent properties of several polypropylene spunbond/meltblown/spunbond ("SMS") webs commercially available from BBA Nonwovens were determined before and after the application of various antistatic and/or fabric repellent topical treatments. The topical treatments were applied to the commercially available SMS by conventional means, such as dip coating. The results set forth in Table 1 attached demonstrate the detrimental effect of antistatic topical treatments on the water resistance, i.e., the hydrostatic head, of conventional SMS webs.

Laminates of the Invention

EXAMPLES 1 AND 2

Barrier laminates according to the invention were prepared as described below. A first spunbonded web was formed of polypropylene available from Amoco under the trade designation 7956. The filaments in the first spunbond layer had a denier per filament of about 2 to 3, and the spunbonded web of substantially continuous polypropylene filaments had a basis weight of about 25 gsm. A meltblown web was prepared by meltblowing polypropylene available from Exxon under the trade designation 3746G to give a fibrous web having a basis weight of about 12 gsm onto the surface of the first spunbonded web. A conductive layer was formed by directing 18 denier Grade 18-2-E3N conductive multicomponent nylon/carbon filament from Solutia Chemical Company to form a ply having a basis weight of about 0.23 gsm onto the surface of the meltblown web. A second spunbonded web formed of polypropylene available from Amoco under the trade designation of 7956 was formed on the surface of the conductive layer. The filaments in the second spunbond layer had a denier per filament of about 2 to 3 denier, and the spunbonded web of substantially continuous polypropylene filaments had a basis weight of about 25 gsm.

The webs were bonded together to form a barrier laminate by passing the sample through the nip of a cooperating pair of textured and smooth embossing rolls.

The antistatic and fluid repellent properties of a web formed in accordance with the invention was determined before and after the application of topical fluid repellent. The results set forth in Table 2 attached demonstrate the beneficial balance of antistatic and fluid repellent properties provided by the barrier laminates of the invention.

As indicated in Table 2, the barrier laminates of the invention exhibit a beneficial balance of antistatic performance, alcohol resistance and hydrohead.

Handsheet Examples

Comparative Example 6 was prepared by bonding outer layers of 7657 Polypropylene Spunbond Filaments (2 to 3 denier) ("SB") from Amoco Corp. of Chicago, Ill. to an inner layer of 3746 G Meltblown Polypropylene ("MB") by Exxon Corp. of Houston, Tex. The laminate layers were point bonded by passing the layers through a heated patterned calender. A topical fluid repellent was applied to the sample by immersing it into an aqueous solution containing Bayguard™ LTC, commercially available from Bayer Chemical Corp. of Wellford, S.C., and isopropanol. The Bayguard™ was present in the aqueous solution in an amount of about 2 weight percent, based on the weight of the solution ("bos"). The isopropanol was present in the aqueous solution in an amount of about 4 weight percent, bos. The sample was immersed in the topical fluid repellent for about 2 to 3 seconds until it became saturated. The saturated sample was then calendered to reduce the wet pick up of topical fluid repellent to between 60 to 80% of dry web weight. The calendered web was then dried and cured at 265 to 270° F. for 3 minutes.

for the barrier laminate, resulting in an increased hydrohead value.

The foregoing examples are illustrative of the present invention and are not to be construed as limiting thereof. The invention is defined by the following claims, with equivalents of the claims to be included therein.

TABLE 1

Antistatic and Fluid Repellency of Various Commercially Available Polypropylene SMS Barrier Laminates

| Sample | SMS Id | Nominal Basis Weight (gsm) | Topical Antistat | Topical Fluid Repellent | Hydrohead[1] (cm) | Alcohol Repellency[2] (% Isopropanol) | Static Decay Time (sec)[3] |
|---|---|---|---|---|---|---|---|
| Comp. Ex. 1 | BBA T0831D | 55 | No | No | 72 | 1–2 | >60 |
| Comp. Ex. 2 | BBA T0832D[9] | 55 | Yes[4] | Yes[5] | 44 | 8–9 | 0.254 |
| Comp. Ex. 3 | BBA T0813D | 50 | No | No | 62 | 1–2 | >60 |
| Comp. Ex. 4 | BBA T0813D | 50 | No | Yes[6] | 65 | 8–9 | >60 |
| Comp. Ex. 5 | BBA T0618D | 50 | Yes[7] | Yes[8] | N/A | 8–9 | 0.49 |

[1]Determined per International Nonwovens and Disposables Association ("INDA") Test Method IST 80.6 (98).
[2]Determined per INDA Test Method IST 80.8 (95).
[3]Determined per INDA Test Method IST 40.2 (92), indicating the average amount of time required for an initial negative static charge and subsequent positive static charge to dissipate from 5000 V to 500 V.
[4]The topical antistat was applied by Precision Fabric Group ("PFG") of Greensboro, NC. The composition of the treatment chemicals are proprietary to PFG.
[5]The alcohol repellant was was applied by Precision Fabric Group of Greensboro, NC. The composition of the treatment chemicals are proprietary to PFG.
[6]The fluid repellant was Baygaurd LTC commercially available from Bayer Chemicals, Wellford, SC, present on the barrier laminate at 1.3 wt %, based on the weight of the laminate.
[7]The topical antistat was applied by Precision Fabric Group of Greensboro, NC. The composition of the treatment chemicals are proprietary to PFG
[8]The fluid repellant was Baygaurd LTC commercially available from Bayer Chemicals, Wellford, SC, present on the barrier laminate at 1.3 wt %, based on the weight of the laminate.
[9]BBA grade T0832D is a version of grade T0831D that has been topically treated by PFG for antistat and fluid repellency.

Example 3 was prepared using the methods and materials of Comparative Example 6, except that a conductive layer was formed between the bottom spunbond layer and the meltblown layer prior to bonding. The conductive layer was formed by depositing 1 end of 18 denier No-Shock Grade 18-2-E3N from Solutia of Gonzalez, Fla. onto a first spunbond layer to form a 0.23 gsm layer. The conductive layer was then point bonded to the first spunbond layer by calendering. The meltblown layer was then applied to the conductive layer, and the three layer laminate was calendered. A second spunbond layer was superposed upon the bonded meltblown layer and the resulting four layer laminate was calendered to form a barrier laminate in accordance with the invention.

Table 3 indicates the superior static decay time provided by the barrier laminates of the invention without detriment to the fluid repellent properties, e.g. the hydrohead and alcohol repellency. As shown in Table 3, the conductive layer of the invention may actually increase the hydrohead value of the resulting barrier laminate. Applicants hypothesize that the conductive layer may provide reinforcement

TABLE 2

Antistatic and Fluid Repellency of Barrier Laminates Formed in Accordance with the Present Invention

| Sample | Basis Weight (gsm) | Topical Antistat | Topical Alcohol Repellent | Static Decay Time for Negative Charges (sec)[3] |
|---|---|---|---|---|
| Example 1 | 72 | No | No | 0.01 |
| Example 2 | 72 | No | Yes[4] | — |

[1]Determined per International Nonwovens and Disposables Association ("INDA") Test Method IST 80.6 (98).
[2]Determined per INDA Test Method IST 80.8 (95).
[3]Determined per INDA Test Method IST 40.2 (92), based on time to dissipate negative charges only.
[4]The fluid repellent was applied by Precision Fabric Group ("PFG") of Greensboro, NC. The composition of the treatment chemicals are proprietary to PFG.

TABLE 3

Beneficial Properties of Comparable Handsheet Samples

| Sample | Basis Weight (gsm) | | | | Topical Alcohol Repellent | Hydrohead[1] (cm) | Alcohol Repellency[2] (% Isopropanol) | Static Decay Time[3] | |
|---|---|---|---|---|---|---|---|---|---|
| | Top SB | MB | Conductive Layer | Bottom SB | | | | −5 kV to −0.5 Kv | +5 kV to +0.5 Kv |
| Comp. Ex 6 | 25 | 12 | 0 | 25 | 1.05 | 64 | 80 | >60 secs | >60 secs |
| Example 3 | 25 | 12 | 0.23 | 25 | 0.81 | 79 | 80 | 0.01 | 0.06 |

[1] Determined per International Nonwovens and Disposables Association ("INDA") Test Method IST 80.6 (98).
[2] Determined per INDA Test Method IST 80.8 (95).
[3] Determined per INDA Test Method IST 40.2 (92), indicating the average amount of time required for a negative static charge and a positive static charge to dissipate from 5000 V to 500 V, respectively.

That which is claimed is:

1. A nonwoven barrier laminate comprising
   (a) outer spunbonded layers;
   (b) at least one hydrophobic microporous layer between the outer spunbonded layers;
   (c) at least one discrete conductive layer comprising electrically conductive strands, the strands being arranged randomly within the conductive layer; and
   (d) a multiplicity of discrete bond sites bonding together said layers to form a coherent fabric.

2. A nonwoven barrier laminate according to claim 1 wherein said electrically conductive strands are selected from the group consisting of carbon filaments and metallic filaments.

3. A nonwoven barrier laminate according to claim 1 wherein said electrically conductive strands comprise multicomponent fibers or filaments having at least one nonconductive polymer component and at least one conductive component.

4. A nonwoven barrier laminate according to claim 1 wherein said electrically conductive strands comprise monocomponent filaments formed from a polymer containing a conductive melt-additive.

5. A nonwoven barrier laminate according to claim 1 wherein said conductive layer comprises from about 0.1 to 0.5 weight percent of the barrier laminate.

6. A nonwoven barrier laminate according to claim 1 wherein said conductive layer has a basis weight ranging from about 0.01 to 0.5 gsm.

7. A nonwoven barrier laminate according to claim 1, wherein said conductive layer has a basis weight of about 0.2 gsm.

8. A nonwoven barrier laminate according to claim 1 wherein said laminate has a static decay time of about 0.10 seconds or less for a negative charge to dissipate from 5000V to 500V.

9. A nonwoven barrier laminate according to claim 8, wherein said laminate has a hydrohead of at least about 35 cm and alcohol repellency of about 6.0 or more.

10. A nonwoven barrier laminate according to claim 1, wherein said hydrophobic microporous layer comprises meltblown fiber.

11. A nonwoven barrier laminate according to claim 1, wherein said spunbond layers and hydrophobic microporous layer comprise polypropylene filaments.

12. A nonwoven barrier laminate comprising
   (a) outer spunbonded layers comprising substantially continuous thermoplastic filaments;
   (b) at least one hydrophobic microporous layer comprising meltblown microfibers between the outer spunbonded layers;
   (c) at least one discrete conductive layer comprising electrically conductive filaments located between one of said outer spunbond layers and said at least one hydrophobic microporous layer, the conductive filaments being randomly arranged within the conductive layer; and
   (d) a multiplicity of discrete point bond sites bonding together said layers to form a coherent fabric.

13. A nonwoven barrier laminate according to claim 12, wherein said outer spunbond layers and said meltblown microfibers are polypropylene.

14. A nonwoven barrier laminate according to claim 12, wherein said electrically conductive filaments comprise multicomponent filaments including at least one nonconductive polymer component and at least one electrically conductive component.

15. A nonwoven barrier laminate according to claim 12, wherein said outer spunbond layers are treated with a topical fluid repellant composition.

* * * * *